United States Patent [19]

Fujiwa et al.

[11] Patent Number: 5,631,342

[45] Date of Patent: May 20, 1997

[54] LACTONE-MODIFIED DIKETENE(METH) ACRYLATE COMPOUND, A PROCESS FOR THE PREPARATION THEREOF, AND A (CO) POLYMER

[75] Inventors: Takaaki Fujiwa, Otake; Tomohisa Isobe, Iwakuni, both of Japan

[73] Assignee: Daicel Chemical Industries, Ltd., Tokyo, Japan

[21] Appl. No.: 562,113

[22] Filed: Nov. 22, 1995

Related U.S. Application Data

[62] Division of Ser. No. 333,062, Nov. 1, 1994, Pat. No. 5,516,933.

[30] Foreign Application Priority Data

| Nov. 1, 1993 | [JP] | Japan | 5-273830 |
| Feb. 28, 1994 | [JP] | Japan | 6-29615 |
| Sep. 1, 1994 | [JP] | Japan | 6-208862 |

[51] Int. Cl.$^6$ ............................................. C08G 18/10
[52] U.S. Cl. ............................. 528/75; 528/227; 528/229
[58] Field of Search ........................ 528/75, 227, 229

[56] References Cited

U.S. PATENT DOCUMENTS

| 3,117,156 | 1/1964 | Keller et al. |
| 3,459,790 | 8/1969 | Smith |
| 4,296,226 | 10/1981 | Braun et al. |
| 4,346,231 | 8/1982 | Ponticello et al. |
| 4,418,207 | 11/1983 | Braun et al. |
| 4,916,254 | 4/1990 | Watanabe et al. |

*Primary Examiner*—Joseph L. Schofer
*Assistant Examiner*—N. Sarofim
*Attorney, Agent, or Firm*—Morgan & Finnegan, LLP

[57] ABSTRACT

Disclosed are a novel lactone-modified diketene (meth) acrylate compound having an active methylene group in the molecule and a process for the preparation thereof.

The novel lactone-modified diketene(meth)acrylate compound of the present invention can be preferably used as resins for coatings, adhesives, inks, photosensitive materials for photographs, dispersants for pigments, agents for processing fibers, and modifiers for rubbers.

Furthermore, disclosed is a novel (co)polymer which comprises the novel lactone-modified diketene(meth)acrylate compound and, optionally, a polymerizable monomer having an ethylenically unsaturated double bond.

Still further, disclosed is a curable composition which comprises a lactone-modified diketene(meth)acrylate compound and at least one selected from the group consisting of a melamine, an isocyanate, and aldehyde, and an amine.

1 Claim, 6 Drawing Sheets

LACTONE-MODIFIED DIKETENE(METH) ACRYLATE COMPOUND, A PROCESS FOR THE PREPARATION THEREOF, AND A (CO) POLYMER

This is a divisional of application Ser. No. 08/333,062, filed Nov. 1, 1994 now U.S. Pat. No. 5,516,933.

FIELD OF THE INVENTION

The present invention relates to a novel lactone-modified diketene(meth)acrylate compound having an active methylene group in the molecule and to a process for the preparation thereof.

The novel lactone-modified diketene(meth)acrylate compound of the present invention can be preferably used as resins for coatings, adhesives, inks, photosensitive materials for photographs, dispersants for pigments, agents for processing fibers and modifiers for rubbers.

The novel lactone-modified diketene(meth)acrylate compound of the present invention also has a terminal acetylacetonate group in the molecule.

Furthermore, the present invention relates to a novel (co)polymer which comprises the lactone-modified diketene (meth)acrylate compound and, optionally, a polymerizable monomer having an ethylenically unsaturated double bond.

BACKGROUND OF THE INVENTION

Hitherto, an acetoxyethyl methacrylate has been well known as a (meth)acrylate having a terminal acetylacetonate group in the molecule.

The acetoxyethyl methacrylate is represented by the following formula (III):

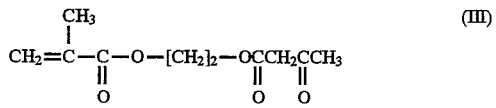

U.S. Pat. No. 3,459,790 describes that the above-described compound (III) can be prepared by the reaction of 2-hydroxyethyl methacrylate with diketene, and the compound can be copolymerized with butyl acrylate, acrylic acid, etc., to obtain an acrylic copolymer having active protons.

U.S. Pat. No. 3,459,790 further describes that the acrylic copolymer can be used as a photosensitive material in the photographic field exhibiting a good dimensional stability and abrasion resistance.

On the other hand, U.S. Pat. No. 4,288,511 describes that the acrylic copolymer can be used in the photographic field as a hydrophilic vehicle for chelating acid dyes or dyeforming materials to provide a metallized dye image.

Still further, Japanese Unexamined Patent Publication (Kokai) 275356/1986 describes that the acrylic copolymer can be used as a photosensitive resin composition for resist by mixing with a polyacrylic acid, methyl methacrylate, trimethylolpropane triacrylate, and a photo-initiator, etc., Japanese Unexamined Patent Publication (Kokai) 156225/1993 also describes that the acrylic copolymer can be used as one liquid for a two-liquid adhesive by mixing with Epikote 828 which is a typical epi-bis epoxy resin.

Although the acetoxyethyl methacrylate represented by the formula (III) has the property of providing an excellent reactivity as a dispersant for pigments and inks, etc., it must be further improved in flexibility, anti-strippability from a substrate, compatibility with other polymers, and resistance to scratches.

On the other hand, requirements have recently begun to arise in the development of monomers and resins necessitating that they have more excellent characteristics and higher quality from the viewpoint of saving energy, preserving resources, and diversifying applications.

More specifically, there have been proposed monomers or polymers having a higher stability and higher sensitivity in the field of photosensitive materials, and water-based coatings, high-solid coatings, and UV-curable coatings in the field of coatings.

A (meth)acrylic copolymer obtained by the radical copolymerization of acetoxyethyl (meth)acrylate, acrylic acid, styrene, etc., is employed as adhesives or coatings for woodworking by being used together with a curing agent such as amines, for example.

Such adhesives or coatings are insufficient in stress relaxation during adhering and curing, resulting in considerably poor adhesion, however, and the resultant stripping of the coating layer from a substrate.

Furthermore, the copolymer is employed as coatings having weatherability, chemical resistance, water resistance, contamination resistance, and excellent curability by being used together with a curing agent such as isocyanates, melamines, etc.

It is difficult, however, for the copolymer to provide sufficiently flexible coating layers.

As described hereinabove, although the acetoxyethyl methacrylate monomer can be employed in various fields because of its unique reactivity, it has the disadvantages of insufficient flexibility, poor adhesion, abrasion resistance, compatibility with other resins, and stress relaxation, and these advantages must be improved.

In addition, in the case that it is employed as photosensitive material or dispersants for pigments in the form of emulsion, the acetoxyethyl methacrylate monomer is insufficient in its affinity to pigments and compatibility with other resins.

For the purpose of solving the above-mentioned disadvantages, as a result of an intensive investigation, the inventors of this invention have now found that it is possible to solve the problems by modifying a lactone-modified (meth)acrylate compound with diketene.

SUMMARY OF THE INVENTION

It is an object of the present invention to provide a novel lactone-modified diketene(meth)acrylate compound and a (co)polymer therefrom having excellent flexibility, anti-strippability, abrasion resistance, compatibility with other resins, and stress relaxation in coated layers or emulsions.

A first aspect of the present invention relates to a lactone-modified diketene(meth)acrylate compound represented by the following general formula (I):

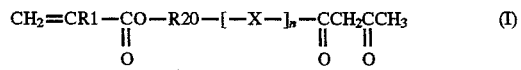

wherein R1 is hydrogen or a methyl group, R2 is a hydrocarbon residual group having a carbon number of ranging from 1 to 10, n is an integer ranging from 1 to 20, and X is a structural unit derived from the ring opening reaction of a lactone compound represented by the following formula:

$$-\underset{\underset{O}{\|}}{C}-(\underset{\underset{Rb}{|}}{C})_z-O-$$

wherein z is an integer ranging from 4 to 8, and Ra and Rb are each an independent hydrogen atom or a methyl group.

A second aspect of the present invention relates to a process for the preparation of a process for the preparation of the lactone-modified diketene (meth)acrylate compound.

A third aspect of the present invention relates to a (co) polymer which comprises (co)polymerization of the lactone-modified diketene(meth)acrylate compound and, optionally, a polymerizable monomer having an ethylenically unsaturated double bond.

The (co)polymer prepared by the (co)polymerization of the lactone-modified diketene(meth)acrylate compound has side chains in which lactone units are introduced. The amount of lactone units can be widely controlled so that there can be provided various resins having a wide range of flexibility, adhesion ability, and glass transition temperatures which can be employed in various uses.

Furthermore, surprisingly, the lactone-modified diketene (meth)acrylate compound can be improved even more in reactivity with, for example, a curing agent than the acetoxyethyl methacrylate represented by the above-mentioned general formula (III).

It appears that the improvement in reactivity would depend upon the mobility of the acetoacetic ester group therein because of the situation of its distance from its main chain due to the introduced lactone units.

DETAILED DESCRIPTION OF THE INVENTION

Figure 1:
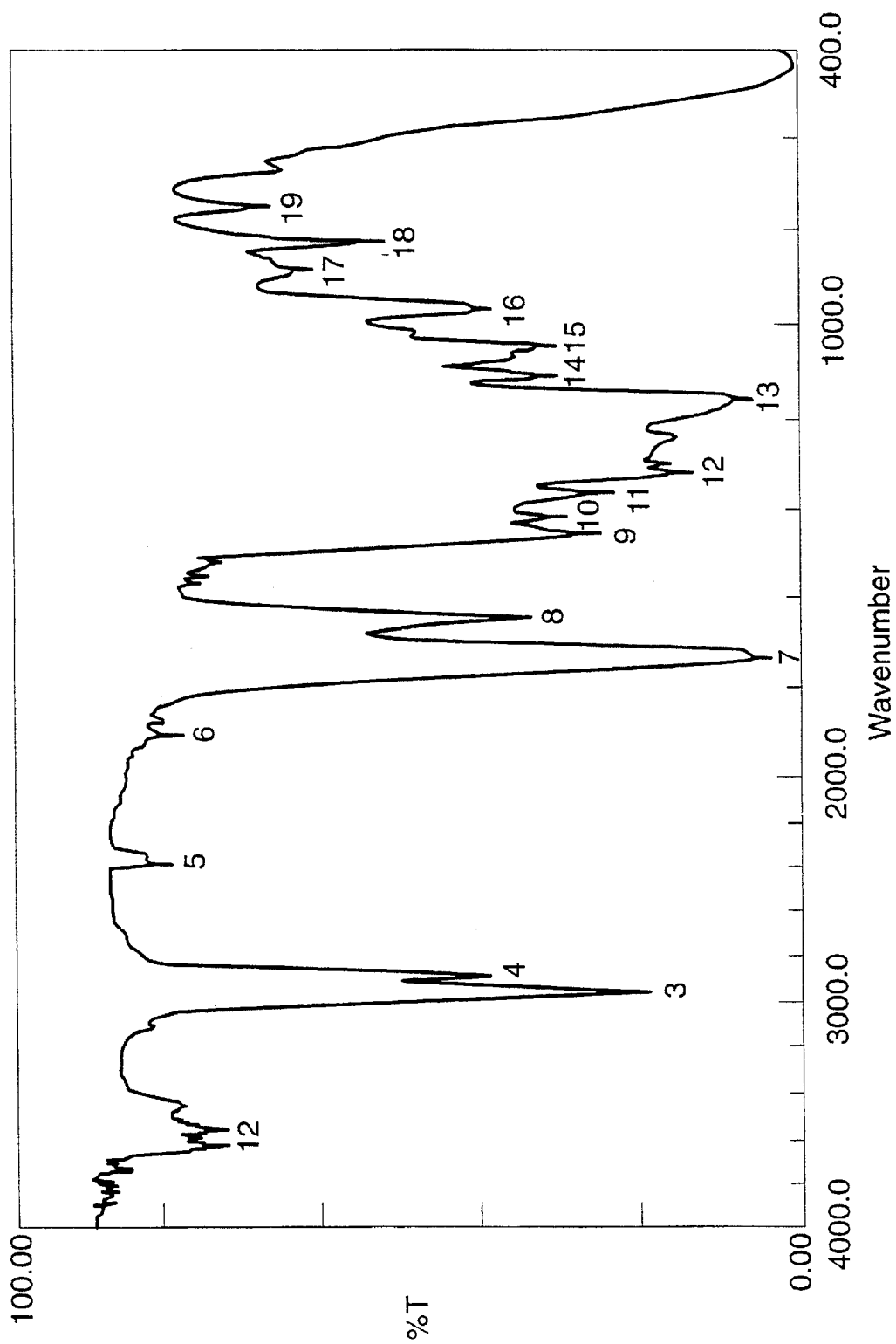
FIGS. 1, 2, and 3 are an IR spectra chart, a 1H-NMR spectra chart, and a GPC chart related to the epsilon-caprolactone-modified diketene methacrylate compound obtained in Example 1, respectively.

The present invention will be described hereinafter in more detail.

According to a first aspect of the present invention, there is provided a lactone-modified diketene(meth)acrylate compound represented by the following general formula (I):

$$CH_2=CR1-\underset{\underset{O}{\|}}{C}O-R2O-[-X-]_n-\underset{\underset{O}{\|}}{C}CH_2\underset{\underset{O}{\|}}{C}CH_3 \quad (I)$$

wherein R1 is hydrogen or a methyl group, R2 is a hydrocarbon residual group having a carbon number ranging from 1 to 10, n is an integer ranging from 1 to 20, and X is a structural unit derived from the ring opening reaction of a lactone compound represented by the following formula:

$$-\underset{\underset{O}{\|}}{C}-(\underset{\underset{Rb}{|}}{C})_z-O-$$

wherein z is an integer ranging from 4 to 8, and Ra and Rb are each an independent hydrogen atom or a methyl group.

According to a second aspect of the present invention, there is provided a process for the preparation of the lactone-modified diketene(meth)acrylate compound.

The lactone-modified diketene(meth)acrylate compound of the present invention can be prepared by the reaction of a compound represented by the following general formula (II):

$$CH_2=CR1-\underset{\underset{O}{\|}}{C}O-R2O-[-X-]_n-H \quad (II)$$

wherein R1 is hydrogen or a methyl group, R2 is a hydrocarbon residual group having a carbon number ranging from 1 to 10, n is an integer ranging from 1 to 20, preferably from 1 to 10, and X is a structural unit derived from the ring opening reaction of a lactone compound represented by the following formula:

$$-\underset{\underset{O}{\|}}{C}-(\underset{\underset{Rb}{|}}{C})_z-O-$$

wherein z is an integer ranging from 4 to 8, and Ra and Rb are each an independent hydrogen atom or a methyl group; with a diketene compound.

In the general formulae (I) and (II), R1 is hydrogen or a methyl group, R2 is a hydrocarbon residual group having a carbon number ranging from 1 to 10, n is an integer ranging from 1 to 20, preferably from 1 to 10, and X is a structural unit derived from the ring opening reaction of a lactone compound represented by the following formula:

$$-\underset{\underset{O}{\|}}{C}-(\underset{\underset{Rb}{|}}{C})_z-O-$$

wherein z is an integer ranging from 4 to 8, and Ra and Rb are each independently hydrogen atom or a methyl group.

In the case where n exceeds 20, a polymer prepared by the (co)polymerization of the lactone-modified diketene(meth) acrylate compound represented by the following general formula (I) would become excessively soft, and, in contrast, in the case when n is below 1, the reactivity in the acetoacetoxy(meth)acrylic group cannot be improved because amounts of lactone units are too few.

In the structural unit X, Ra and Rb are each an independent hydrogen atom or a methyl group, respectively, which also depend upon the lactone compound to be employed.

For example, in the case of epsilon-caprolactone being employed as the starting lactone compound, both Ra and Rb represent hydrogen.

Further, in the case of beta-methyl-delta-valerolactone being employed as the starting lactone compound, Ra and Rb represent a methyl group or hydrogen, respectively. In addition, in the case when 3-methylcaprolactone is used as a starting lactone compound, Ra and Rb represent a methyl group and hydrogen, respectively.

That is, in the case of epsilon-caprolactone being used as a lactone compound, the unit X in the formulae (I) and (II) is —O—(—CH$_2$—)$_5$—CO—.

In the case of beta-methylgamma-valero-caprolactone being used as a lactone compound, the unit X in the formulae (I) and (II) is

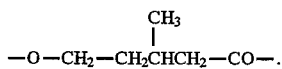

In the case of 3,5,5-trimethylcaprolactone being employed as a lactone compound, the unit X in the formulae (I) and (II) is

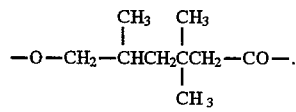

In the case of 3,3,5-trimethylcaprolactone being employed as a lactone compound, the unit X in the formulae (I) and (II) is

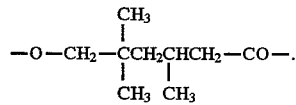

The lactone compound can also be employed as a mixture composed of at least two types of lactones.

The compound represented by the general formula (II) which is a starting material can be prepared by the ring opening reaction of the lactone compound with 2-hydroxyethyl (meth)acrylate which behaves as a ring opening initiator. Typical examples of the lactone-modified 2-hydroxyethyl(meth)acrylate include more specifically, PCL FM-1, PCL FM-2, PCL FM-4, PCL FA-1, PCL FA-2 [manufactured by Daicel Chemical Industries, Ltd.] and Tone M100 and Tone M201 [manufactured by Union Carbide Corporation].

For example, PCL FM-2 is represented by the formula CH$_2$=CCH$_3$—CO—CH$_2$CH$_2$—O—[—CO—(—CH$_2$—)$_5$—O—]$_n$—H, wherein n is 2 on the average.

It is to be noted that the process for the preparation of the PCL FM and FA series is described in U.S. Pat. No. 4,916,254 in detail.

Compounds represented by the general formula (II) also include a lactone-modified 1,4-butanediol monoacrylate, a lactone-modified hydroxypropyl(meth)acrylate, a lactone-modified polyethyleneglycol (meth)acrylate which is prepared by the addition reaction of at least two mols of ethylene oxide with (meth)acrylic acid, a lactone-modified polypropylene-glycol (meth)acrylate which is prepared by the addition reaction of at least two mols of propylene oxide with (meth)acrylic acid.

The reaction for the preparation of the lactone-modified diketene(meth)acrylate compound of the present invention can be carried out at an optional molar ratio of diketene to the compound represented by the general formula (II), preferably from 0.8 to 1.2.

In the case when a large amount of diketene remains in the reaction system after the completion of the reaction, it can be removed by decomposition with water or aqueous alkalis, or by being distilled off, for example, with a thin-layer evaporator, etc.

In the case when the compound represented by the general formula (II) is employed excessively, the unreacted compound can behave as a monomer having an ethylenically unsaturated double bond without any problems.

The reaction is carried out at temperatures ranging from 20° to 140° C., preferably 50° to 100° C., in the presence of catalysts in order to accelerate the reaction.

In the case when the reaction temperature exceeds 140° C., the compound represented by the general formula (II) would become unstable and gelling would occur. In contrast, in the case when it is below 20° C., the reaction velocity would become slow, undesirably resulting in being disadvantageous from the viewpoint of productivity.

Preferred catalysts include Lewis acids typified by metallic compounds. More specifically, zinc compounds, titanium compounds, nickel compounds, cobalt compounds, aluminum compounds and zirconium compounds, etc., can also be employed as catalysts.

Still further, tertiary amines such as triethyl amine and tributyl amine, etc., can also be employed as catalysts.

Catalysts are employed in the amount ranging from 5–6 ppm to 2000–3000 ppm, preferably ranging from 200–300 ppm to approximately 1000 ppm.

Solvents may or may not be employed. Preferred examples of solvents specifically include esters, aromatic compounds, and halogenated compounds which do not have active hydrogens, in order to prevent a reaction between active methylene and active hydrogens.

The reaction can preferably be carried out in the presence of polymerization inhibitors such as hydroquinone, hydroquinone monomethylether which are phenols, phenothiazine which is a sulphur compound, N-methylnitroso aniline, etc., which is a nitrosocompound, and phosphorus compounds. One or more of these may be employed.

The amount of the initiator to be used ranges from 5–6 ppm to 2000–3000 ppm. In addition to the initiator, air or a mixed gas composed of nitrogen and oxygen is preferably employed in order to ensure that a stable reaction occurs.

It is to be noted that the streaming amount of air or the mixed gas should be controlled within a range which prevents the formation of an explosive atmosphere.

According to a third aspect of the present invention, there is provided a (co)polymer which comprises a lactone-modified diketene(meth)acrylate compound represented by the following general formula (I):

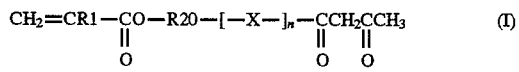 (I)

wherein R1 is hydrogen or a methyl group, R2 is a hydrocarbon residual group having a carbon number ranging from 1 to 10, n is an integer ranging from 1 to 20 and, X is a structural unit derived from the ring opening reaction of a lactone compound represented by the following formula:

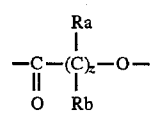

wherein z is an integer ranging from 4 to 8, and Ra and Rb are each an independent hydrogen atom or a methyl group; and optionally, a polymerizable monomer having an ethylenically unsaturated double bond.

The (co)polymer can be prepared by the radical (co)polymerization of the lactone-modified diketene(meth) acrylate compound represented by the above-described general formula (I) in the presence or absence of the polymerizable monomer.

The molar ratio of the lactone-modified diketene(meth)acrylate compound with respect to the polymerizable monomer ranges from 100/0 to 1/99, preferably from 90/10 to 10/90.

In the case when the molar ratio is below 1, the use of the lactone-modified diketene(meth)acrylate compound is substantially meaningless.

In the meantime, it is to be noted that the acetoacetic group reacts with metals by chelating as described below:

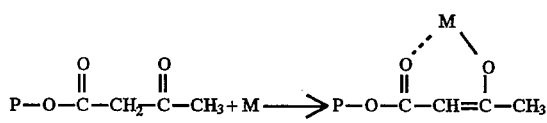

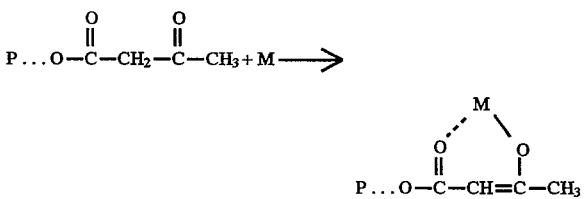

wherein P is a polymer chain and M represents metal.

It is to be noted that an acetoacetic group at a great distance from its main chain shows a more excellent reactivity in the chelating reaction.

As a result, it appears that a coating layer prepared by the (co)polymer can be improved in adhesive strength to a substrate such as metal plates.

In the case when lactone units are present in the (co)polymer, chelating is represented as follows:

wherein P is a polymer chain, M represents metal, and "..." represents lactone units.

In view of chelating, it appears that an adhesive strength to a substrate can be maintained without residual strain by the absorption of stress due to lactone chains during a reaction with a curing agent.

Furthermore, considering chelating, it appears that an acrylic (co)polymer chelated by a metal such as copper or tin, etc., can be formed.

Such a (co)polymer can be used as a material having a property of gradually discharging metal ions, for example, such as coatings for ship bottoms for the purpose of preventing (micro)organisms from taking up residence thereon.

Still further, the (co)polymer has the advantage of excellent resistance to water compared to conventional polyester polyols which contain ester bonds having a tendency toward hydrolysis.

The fact depends upon the reason why ester bonds derived from lactone compounds have a most excellent resistance to hydrolysis.

Accordingly, a (co)polymer emulsion prepared by emulsion (co)polymerization with acrylic acid or acrylates can be employed as an emulsifier for photographs in the presence of emulsifiers and sodium dihyposulfate.

In addition, the active methylene unit in the acetoacetic ester group can react with a melamine, an isocyanate, an aldehyde, and an amine, and the like. The active methylene unit can further react with a compound having double bonds by a Michael addition reaction in an alkali condition to form a crosslinked structure as described below:

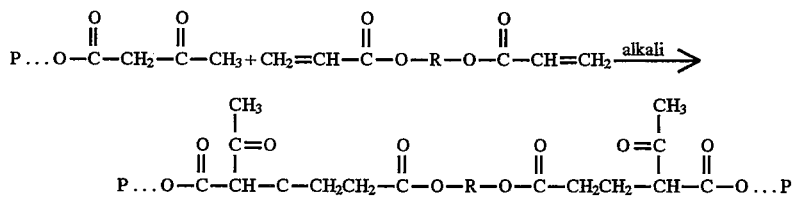

wherein P is a polymer chain and "..." represents lactone units.

Accordingly, the compound (I) of the present invention is useful for coatings or adhesives containing a new curing mechanism by using the above-described reaction. It can be employed, for example, as coatings for cars, varnishes for woodworking, and gravure inks and the like, as well as conventional reactions of a melamine or an isocyanate with polyols.

Moreover, it can be employed for the preparation of a photo-curable resin, more specifically, a resin for printed circuit boards and the advanced processing of metals, and the like using together with an organic halogenated compound, a polymer capable of forming film, and a photosensitive accelerator, and the like.

Generally speaking, the photo-curing process can provide cured coating layers or inks within a short period of time, resulting in the saving of energy and contributing considerably to productivity.

Accordingly, photo-curable coatings are useful as coatings for woodworking, inks for offset printing, and a resist material for the use in the electronics field. These coating layers are rigid, however, and further stress relaxation cannot be made in the cured coating layers because of curing within a short time of period, resulting in cracks on the surface.

The compound (I) and the (co)polymer therefrom of the present invention have lactone units introduced into them, resulting in the solving of the problem.

Examples of ethylenically unsaturated monomer to be optionally employed in the present invention include a conventional vinyl monomer such as styrene, 2-methyl styrene, vinyl acetate, and vinyl chloride, acrylic acid, methacrylic acid, acrylic alkyl esters such as methyl (meth)acrylate, ethyl (meth)acrylate, propyl (meth)acrylate, butyl (meth)acrylate, pentyl (meth)acrylate, hexyl (meth)acrylate, and a (meth)acrylate having hydroxyl group such as 2-hydroxyethyl (meth)acrylate, and the like.

Furthermore, (meth)acrylates such as methoxy diethylene glycol (meth)acrylate, ethoxy diethylene glycol(meth)acrylate, isooctyl oxidiethylene glycol(meth)acrylate, phenoxy triethylene glycol(meth)acrylate, methoxy triethylene glycol(meth)acrylate, methoxy polyethylene #400 glycol (meth)acrylate, (meth)acrylates having silyl group or silane groups at terminals, 2-trimethylsilyloxy ethyl(meth)acrylate, (meth)acrylates having epoxy groups at terminal such as glycidyl (meth)acrylate, (meth)acrylic esters of epoxycyclohexane methanol, and acid anhydrides having unsaturated double bond such a maleic anhydride and derivatives thereof can also be employed.

Of these, (meth) acrylic acid, butyl(meth)acrylate, and 2-hydroxyethyl methacrylate, and the like can be preferably employed, because of their capability of being readily obtained at reasonable commercial costs.

Furthermore, they have hydroxyl group or carboxylic group, whereby various curing methods can be employed.

In radical (co)polymerization, there can be employed emulsion (co)polymerization, suspension (co) polymerization, solution (co)polymerization, and bulk (co) polymerization, and the like which have been conventionally employed.

In solution (co)polymerization, there can be employed organic solvents in an amount ranging from 5 to 100% by weight, preferably ranging from 10 to 40% by weight based on the total weight of monomers including the compounds (I).

In the case when the amount exceeds 100% by weight, although the (co)polymerization can be carried out in a stable condition, it would be disadvantageous from the viewpoint of the recovery of solvents.

Temperatures conventionally employed in radical (co) polymerization range from approximately from 30° to 120° C., preferably from 50° to 100° C.

Solvents can be employed without any limitations except bad solvents from starting monomers and a resulting (co) polymer.

Examples of preferred solvents include aromatic hydrocarbons such as benzene, toluene and xylene, alcohols such as methanol, ethanol, propanol and the like, ketones such as acetone, methylethyl ketone, methylisobutyl ketone, and the like, ethers such as diethylether, dibutylether, dioxane, and the like, esters such as ethylacetate, isobutyl acetate, ethyleneglycol monoacetate, propyleneglycol monoalkyl acetate, dipropyleneglycol monoalkyl acetate, amines such as dimethylformamide, dimethylacetoamide, and the like, and halogenated hydrocarbons such as carbon tetrachloride, chloroform, and the like. One or more of these can be employed.

In (co)polymerization, initiators can be employed which are conventional. Examples of preferred initiators include, for example, 2,2'-azobis(2-methylpropionitrile), 2,2'-azobisisobutyronitrile, 2,2'-azobis-(2,4-dimethylvaleronitrile), peroxides such as lauroyl peroxide, di-t-butylperoxide, bis(4-t-butylcyclohexyl peroxicarbonate), t-butyl(2-ethylhexanoate), methylethyl ketone peroxide, benzoyl peroxide, cumenhydroperoxide, and the like. One or more of these can be employed.

The present invention is illustrated below by Examples.

EXAMPLE 1

Acetoacetylation of a lactone-modified hydroxyethyl methacrylate:

A reaction vessel having a capacity of 1000 milliliters and equipped with a stirrer, a reflux condenser, a thermometer, a dropwise funnel, and a tube for supplying nitrogen gas was charged with 514.7 g of Placcel FM-2 (an epsilon caprolactone-modified hydroxyethyl methacrylate manufactured by Daicel Chemical Industries, Ltd.), followed by stirring after charging 0.64 g of dibutyl tindilaurate into the reaction vessel.

126.8 g of diketene was added to the funnel.

Furthermore, 0.3 g of hydroquinone monomethylether was added to the reaction vessel, and air was charged at a speed of 10 milliliters/minute, followed by heating to an internal temperature of 85° to 95° C. in an oil bath.

Successively, diketene in the dropwise funnel was added dropwise to the reaction vessel over a period of approximately 1 hour.

After completion of the above adding, the internal temperature was maintained at 90° C. for 12 hours, followed by cooling to room temperatures to obtain a product. It was confirmed by a gas chromatographic analysis that 0.70% by weight of diketene remained in the product. Furthermore, the hydroxyl value of the product was below 1.0.

It was confirmed that the reaction was nearly quantitatively completed. An infrared analysis was also carried out to obtain a spectra chart as shown in FIG. 1.

The spectra chart exhibits absorption due to acetylacetone group at 1732 cm$^{-1}$.

Figure 2:
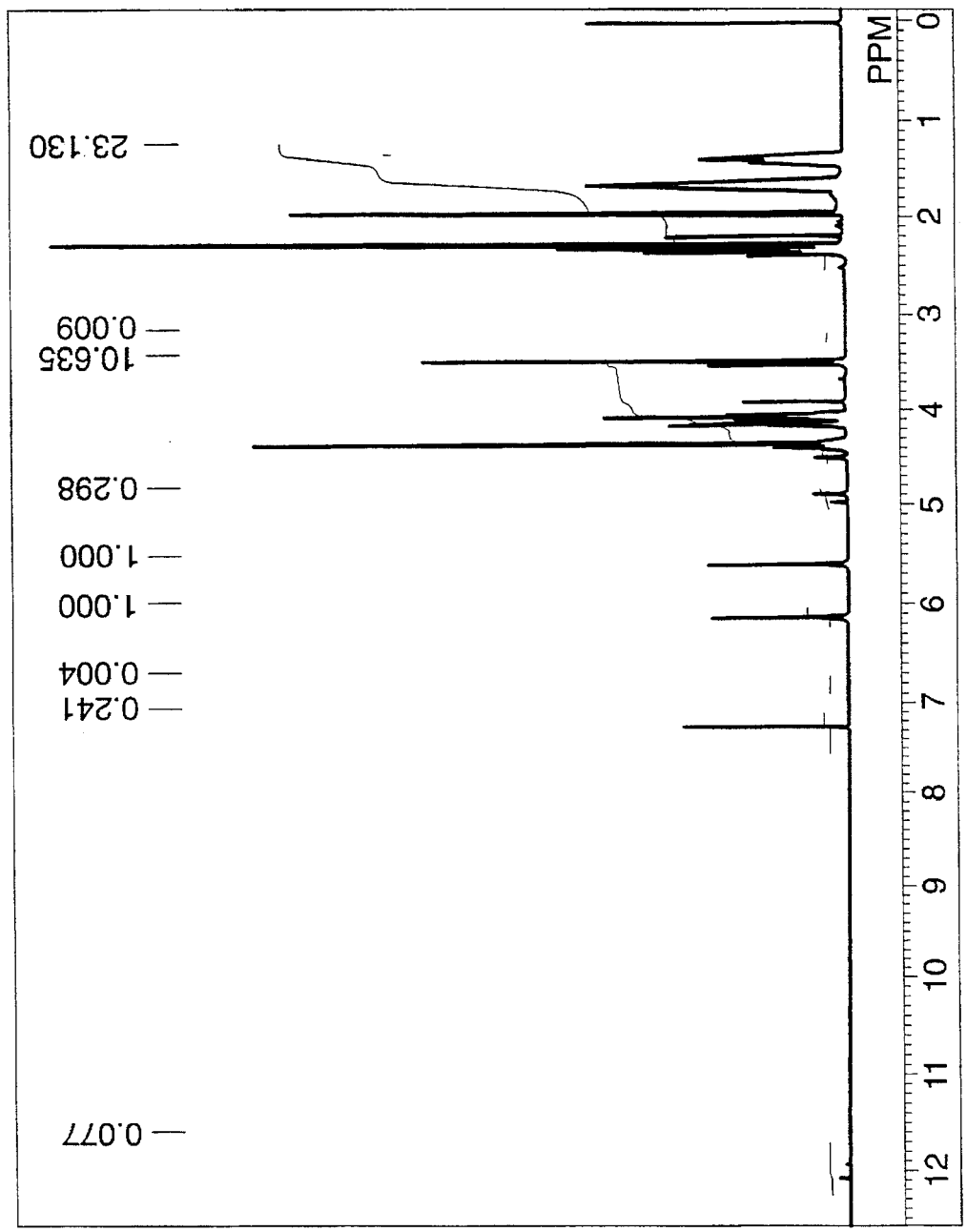

An H-NMR analysis was also carried out to assign values as described below, based on the spectra chart as shown in FIG. 2.

| Delta 1.3–1.45 ppm | Methylene (4H) |
|---|---|
| Delta 1.5–1.7 ppm | Methylene (8H) |
| Delta 1.95 ppm | Methyl (3H) |
| Delta 2.10 ppm | Methyl (3H) |
| Delta 2.2–2.4 ppm | Methylene (4H) |
| Delta 3.4–3.5 ppm | Methylene (1.9H) |
| Delta 4.0–4.18 ppm | Methylene (4H) |
| Delta 4.3–4.4 ppm | Methylene (4H) |
| Delta 5.6 and 6.1 ppm | Methacryl proton (2H) |
| Delta 11.9–12.1 ppm | Enol proton in acetylacetone (2H) |

Figure 3:
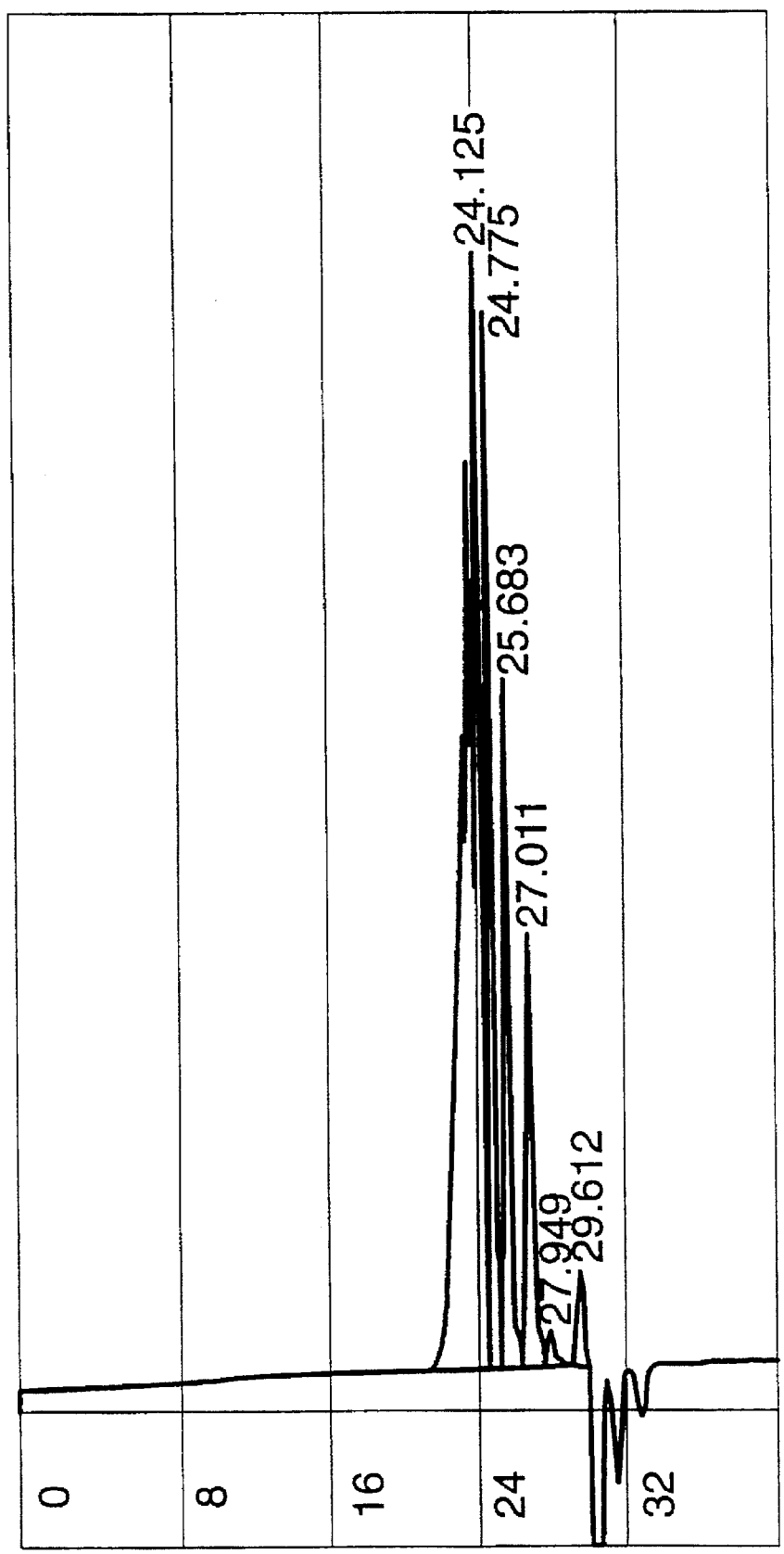

Still further, a GPC analysis was carried out to confirm the distribution of n=0, 1, 2, . . . based on the chart shown in FIG. 3.

Through the above analyses, it was confirmed that the product is a compound having n=average 2, R1=CH$_3$, and R2=—CH$_2$CH$_2$— in the general formula (I) described hereinabove.

EXAMPLE 2

Acetoacetylation of a lactone-modified hydroxyethyl acrylate:

The same procedures as described in Example 1 were repeated except that 151.1 g of Placcel FA-2 (an epsilon caprolactone-modified hydroxyethyl acrylate manufactured by Daicel Chemical Industries, Ltd.), 40.9 g of diketene, and 0.02 g of dibutyl tindilaurate were employed to obtain a product. It was confirmed by gas chromatographic analysis that 0.50% by weight of diketene remained in the product.

Furthermore, the hydroxyl value of the product was below 1.0. It was confirmed that the reaction was nearly quantitatively completed.

Figure 4:
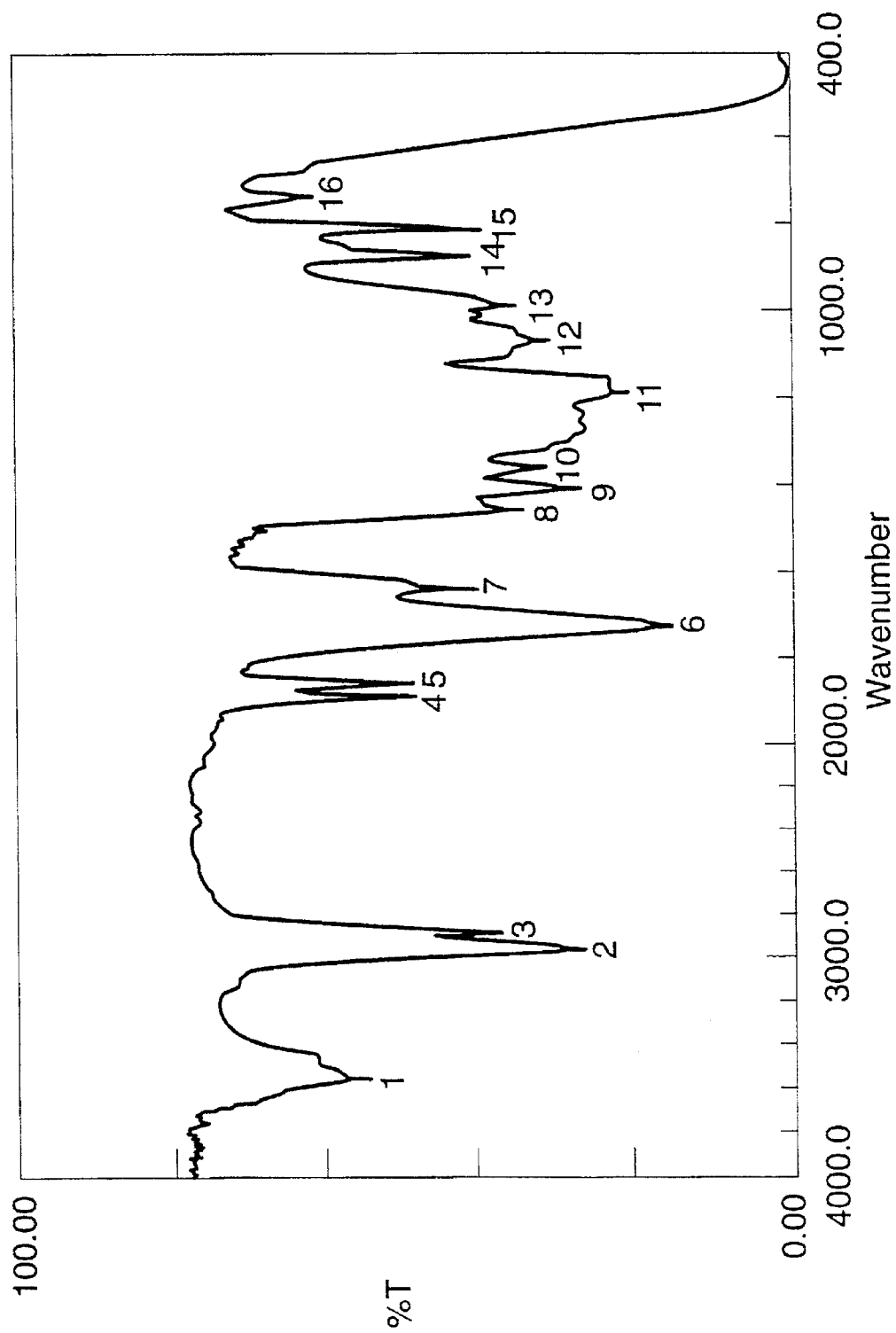
FIGS. 4, 5, and 6 are an IR spectra chart, a 1H-NMR spectra chart, and a GPC chart related to the epsilon-caprolactone-modified diketene acrylate compound obtained in Example 2, respectively.

An infrared analysis was also carried out to obtain a spectra chart as shown in FIG. 4. The spectra chart exhibits an absorption due to acetylacetone group at 1732 cm$^{-1}$.

Figure 5:
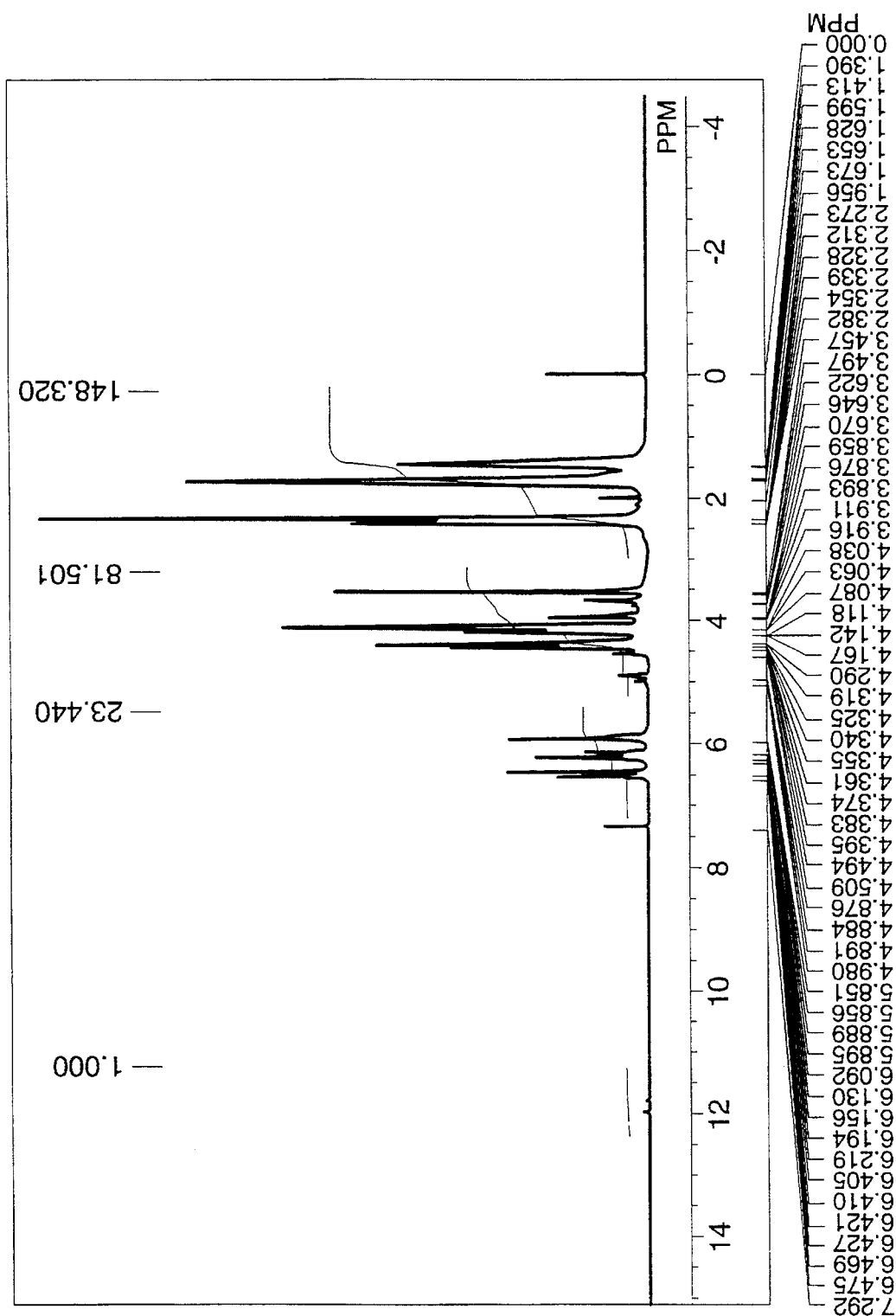

Also, an H-NMR analysis was carried out to assign values as described below based on the spectra chart shown in FIG. 5.

| Delta 1.4 ppm | Methylene (2H) |
|---|---|
| Delta 1.6 ppm | Methylene (8H) |
| Delta 2.2–2.4 ppm | Methyl (3H) |
| Delta 3.3–3.4 ppm | Methylene (1.9H) |
| Delta 4.0–4.2 ppm | Methylene (4H) |

-continued

| | |
|---|---|
| Delta 4.3–4.4 ppm | Methylene (4H) |
| Delta 5.6 and 6.5 ppm | Methacryl proton (3H) |
| Delta 11.9–12.1 ppm | Enol proton in acetylacetone (0.1H) |

Figure 6:
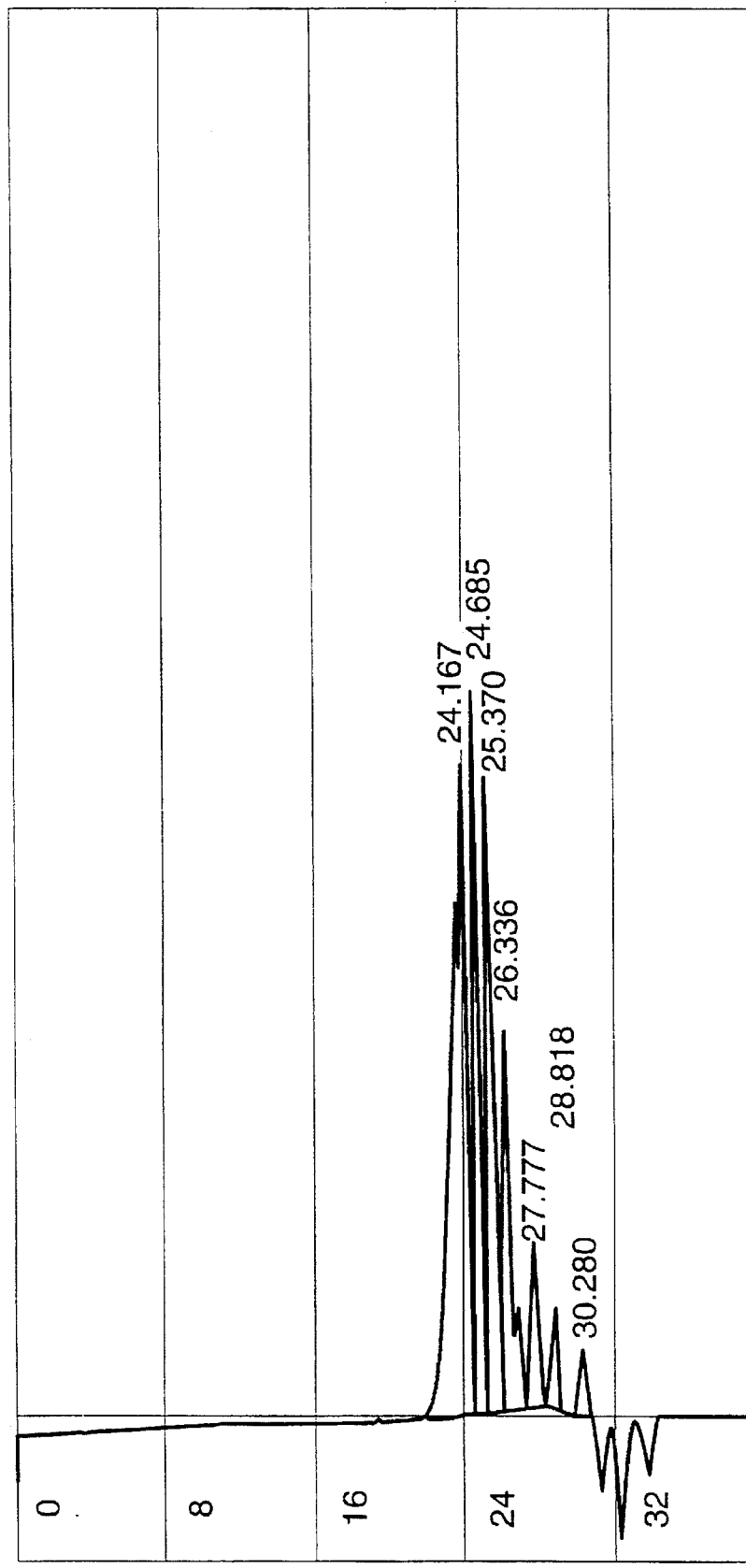

Still further, a GPC analysis was carried out to confirm the distribution of n=0, 1, 2, . . . based on the chart shown in FIG. 6.

Through the above analyses, it was confirmed that the product is a compound having n=average 2, R1=H and R2=—CH$_2$CH$_2$— in the general formula (I) described hereinabove.

EXAMPLE 3

Acetoacetylation of a lactone-modified hydroxyethyl methacrylate:

The same procedures as described in Example 1 were repeated except that 122.0 g of Placcel FM-1 (an epsilon caprolactone-modified hydroxyethyl methacrylate manufactured by Daicel Chemical Industries, Ltd.), 42.0 g of diketene, and 0.01 g of dibutyl tindilaurate were employed.

It was confirmed by gas chromatographic analysis that 0.50% by weight of diketene remained in the product.

Furthermore, the hydroxyl value of the product was below 1.0.

It was confirmed that the reaction was nearly quantitatively completed. The viscosity of the product was 25cp/25° C., and the APHA value was 30.

EXAMPLE 4

Acetoacetylation of a lactone-modified hydroxyethyl acrylate:

The same procedures as described in Example 1 were repeated except that 115.0 g of Placcel FA-1 (an epsilon caprolactone-modified hydroxyethyl methacrylate manufactured by Daicel Chemical Industries, Ltd.), 37.9 g of diketene, and 0.01 g of dibutyl tindilaurate were employed.

It was confirmed by gas chromatographic analysis that 0.30% by weight of diketene remained in the product.

Furthermore, the hydroxyl value of the product was below 1.0.

It was confirmed that the reaction was nearly quantitatively completed. The viscosity of the product was 28cp/25° C., and the APHA value was 20.

EXAMPLE 5

Radical copolymerization of a lactone-modified diketene methacrylate with unsaturated polymerizable monomers:

A reaction vessel having a capacity of 12 liters equipped with a stirrer, a reflux regulator, a thermometer, and a tube for supplying nitrogen gas was charged with 5040 g of ethanol, 560 g of acetone, 1440 g of methylmethacrylate, 480 g of methacrylic acid, and the product obtained in Example 1.

Successively, the reaction vessel was placed at 60° C. in a water bath thermostatically controlled, followed by adding 12.0 g of 2,2'-azobis(2-methylpropionitrile), while streaming nitrogen gas through the reaction vessel. The reaction vessel was maintained at 60° C. for 16 hours to obtain a viscous solution having a viscosity of 900 poise.

50 g of the viscous solution obtained was charged into a round bottomed flask. Successively, the round-bottomed flask was placed at a rotary evaporator to gradually remove solvents at 100° C. in a reduced pressure, resulting in obtaining a solid.

The solid was analyzed by an infrared spectrometer.

The infrared spectra were assigned as described below.

| | |
|---|---|
| 3200 cm$^{-1}$ | absorption by OH in a carboxylic group |
| 1706 cm$^{-1}$ | absorption by C=O in a carboxylic group |
| 1715 cm$^{-1}$ | absorption by a methylester group in methacrylic acid unit |
| 1730 cm$^{-1}$ | absorption by a carbonyl group in an acetylacetonate group |

It was confirmed that the copolymer includes carboxylic groups, methylester groups, and acetylacetonate groups.

EXAMPLE 6

Radical emulsion copolymerization of a lactone-modified diketene methacrylate with unsaturated polymerizable monomers:

A reaction vessel having a capacity of 2 liters equipped with a dropwise funnel, an agitator, a reflux regulator, a thermometer, and a tube for supplying nitrogen gas was charged with 500 milliliters of water, 12 milliliters of an aqueous solution containing 40% of Triton 770 which is a dispersant, and a sodium salt of an alkyl arylpolyester sulfate which is an emulsifier to prepare an aqueous solution.

Successively, the dropwise funnel was charged with 250 milliliters of water containing 6.75 milliliters of 4.0% of Triton 770, 150 g of methylmethacrylate, 50 g of methacrylic acid, and 60 g of the product obtained in Example 2.

Furthermore, 1.25 g of potassium persulfate (K$_2$S$_2$O$_8$) which is a radical polymerization initiator was added to the dropwise funnel, and 0.625 g of potassium persulfate (K$_2$S$_2$O$_5$) and 0.625 g of sodium metahydrogen sulfite (Na$_2$S$_2$O$_5$) which is a stabilizer were added to the reaction vessel.

The reaction vessel was heated and maintained at 60° C., followed by dropwise addition of the mixture in the dropwise funnel over a period of 30 minutes to obtain a polymer latex having a solid content of 27%.

Successively, a thin-layer film was prepared from the polymer latex, and it was dried in a circulation heater.

The dried film was analyzed by an infrared spectrometer.

The infrared spectra were assigned as described below.

| | |
|---|---|
| 3200 cm$^{-1}$ | absorption by OH in a carboxylic group |
| 1710 cm$^{-1}$ | absorption by C=O in a carboxylic group |
| 1720 cm$^{-1}$ | absorption by a methylester group in a methacrylic acid unit |
| 1730 cm$^{-1}$ | absorption by a carbonyl group in an acetylacetonate group |

It was confirmed that the copolymer includes carboxylic groups, methylester groups, and acetylacetonate groups.

It is to be noted in the following that GXS270WB was used for the NMR, JASCO FT/IR-5300 was used for IR, and HPLC LC-6A SYSTEM (column: Polystyrene column, solvent: THF) manufactured by Shimadzu Seisakusho, Ltd., was used for GPC.

Comparative Example

The same procedures as described in Example 1 were repeated except that 242.3 g of acetoacetoxyethyl methacrylate was employed to obtain a viscous solution having a viscosity of 1200 poise.

Application Example 1

1000 g of the polymer solution obtained in Example 1 was mixed with 4.2 g of ethylenediamine to obtain a homogeneous solution. The solution was coated on lauan plates having thickness of 3 mm with a coating amount of 100 g/cm². The wood plates were laminated and compressed under the pressure of 3 kgf/cm² for 10 seconds at room temperature. After compression the wood plates were aged for 24 hours, and cut to obtain test pieces. Adhesive strength was measured to obtain an adhesive strength value of 6.2 kgf/cm² based on JIS K6849.

Comparative Application Example 1

The same procedures as described in Application Example 1 were repeated except that 4.38 g of ethylenediamine and the polymer solution obtained in Comparative Example 1 were employed to obtain an adhesive strength value of 3.1 kgf/cm².

While the invention has been described in detail and with reference to specific embodiments thereof, it will be apparent to one skilled in the art that various changes and modifications can be made therein without departing from the spirit and scope thereof.

What is claimed is:

1. A curable composition which comprises a lactone-modified diketene(meth)acrylate compound represented by the following general formula (I):

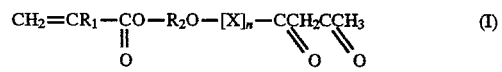

wherein $R_1$ is hydrogen or a methyl group, $R_2$ is a hydrocarbon residual group having a carbon number ranging from 1 to 10, n is an integer ranging from 1 to 20 and X is a structural unit derived from the ring opening reaction of a lactone compound represented by the following formula:

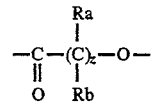

Wherein z is an integer ranging from 4 to 8, and Ra and Rb are each an independent hydrogen atom or a methyl group and at least one selected from the group consisting of a melamine, an isocyanate, an aldehyde, and an amine.

* * * * *